(12) United States Patent
Klein et al.

(10) Patent No.: US 6,581,117 B1
(45) Date of Patent: Jun. 17, 2003

(54) DEVICE AND A METHOD FOR THE AUTOMATIC CONTROL AND ADMINISTRATION OF MEDICAL APPARATUS AND INSTALLATIONS

(75) Inventors: Wolfgang Klein, Rheinstetten (DE); Martin Burger, Oberderdingen (DE); Thomas Belikan, Knittlingen (DE)

(73) Assignee: Richard Wolf GmbH, Knittlingen (DE)

( * ) Notice: Subject to any disclaimer, the term of this patent is extended or adjusted under 35 U.S.C. 154(b) by 0 days.

(21) Appl. No.: 09/496,300

(22) Filed: Feb. 2, 2000

(30) Foreign Application Priority Data

Feb. 2, 1999 (DE) .......................... 199 04 090

(51) Int. Cl.⁷ .......................... G06F 3/00; G06F 13/10; G06F 11/00; A61B 17/00
(52) U.S. Cl. .................. 710/110; 710/104; 710/105; 600/46; 348/65; 700/90; 714/48; 709/251
(58) Field of Search .................. 710/100, 300, 710/305, 110, 104, 105; 600/109, 118, 110, 132, 103, 117, 101, 46; 348/65; 396/374; 700/90; 714/43, 4, 56, 48, 15, 5; 709/222, 227, 208, 251, 252; 606/1, 13, 14; 604/890.1; 713/100

(56) References Cited

U.S. PATENT DOCUMENTS

| | | | |
|---|---|---|---|
| 4,900,301 A | 2/1990 | Morris et al. | |
| 4,989,253 A | 1/1991 | Liang et al. | |
| 5,217,003 A | 6/1993 | Wilk | |
| 5,217,453 A | 6/1993 | Wilk | |
| 5,303,148 A | 4/1994 | Mattson et al. | |
| 5,335,313 A | 8/1994 | Douglas | |
| 5,345,538 A | 9/1994 | Narayannan et al. | |
| 5,368,015 A | 11/1994 | Wilk | |
| 5,544,654 A | 8/1996 | Murphy et al. | |
| 5,627,584 A | * 5/1997 | Nishikori et al. | |
| 5,754,741 A | 5/1998 | Wang et al. | |
| 5,788,688 A | 8/1998 | Bauer et al. | |
| 5,791,908 A | 8/1998 | Gillio | |
| 5,812,397 A | 9/1998 | Pech et al. | |
| 5,910,139 A | 6/1999 | Cochran et al. | |
| 5,970,457 A | 10/1999 | Brant et al. | |
| 6,397,286 B1 | * 5/2002 | Chatenever et al. | |

FOREIGN PATENT DOCUMENTS

| | | |
|---|---|---|
| DE | 693 15 961 T2 | 5/1998 |
| DE | 197 22 221 A1 | 12/1998 |

* cited by examiner

*Primary Examiner*—Gopal C. Ray
(74) *Attorney, Agent, or Firm*—Akin Gump Strauss Hauer & Feld L.L.P.

(57) ABSTRACT

The automatic control and administration of program-controlled endoscopic apparatuses allocated to an operation within an operating theater belonging to a clinic region and connected amongst one another by way of a CAN-bus using the standardized layer-seven CANopen protocol for communication among one another and a master computer, is modified so that with the same CAN-bus, a double ring structure, a ring-star structure and a ring-ring structure may be logically formed, permitting peer-to-peer communication of the apparatuses, with which the apparatuses have equality of access to each other and the master computer. The apparatuses, connected to one another via the CAN-bus, of all operating theaters of a clinic communicate with and are centrally controlled by the master computer. All apparatuses are capable of informing the master computer of the occurring process data or parameters. System operation is possible at the master computer as well as at the apparatuses themselves.

13 Claims, 11 Drawing Sheets

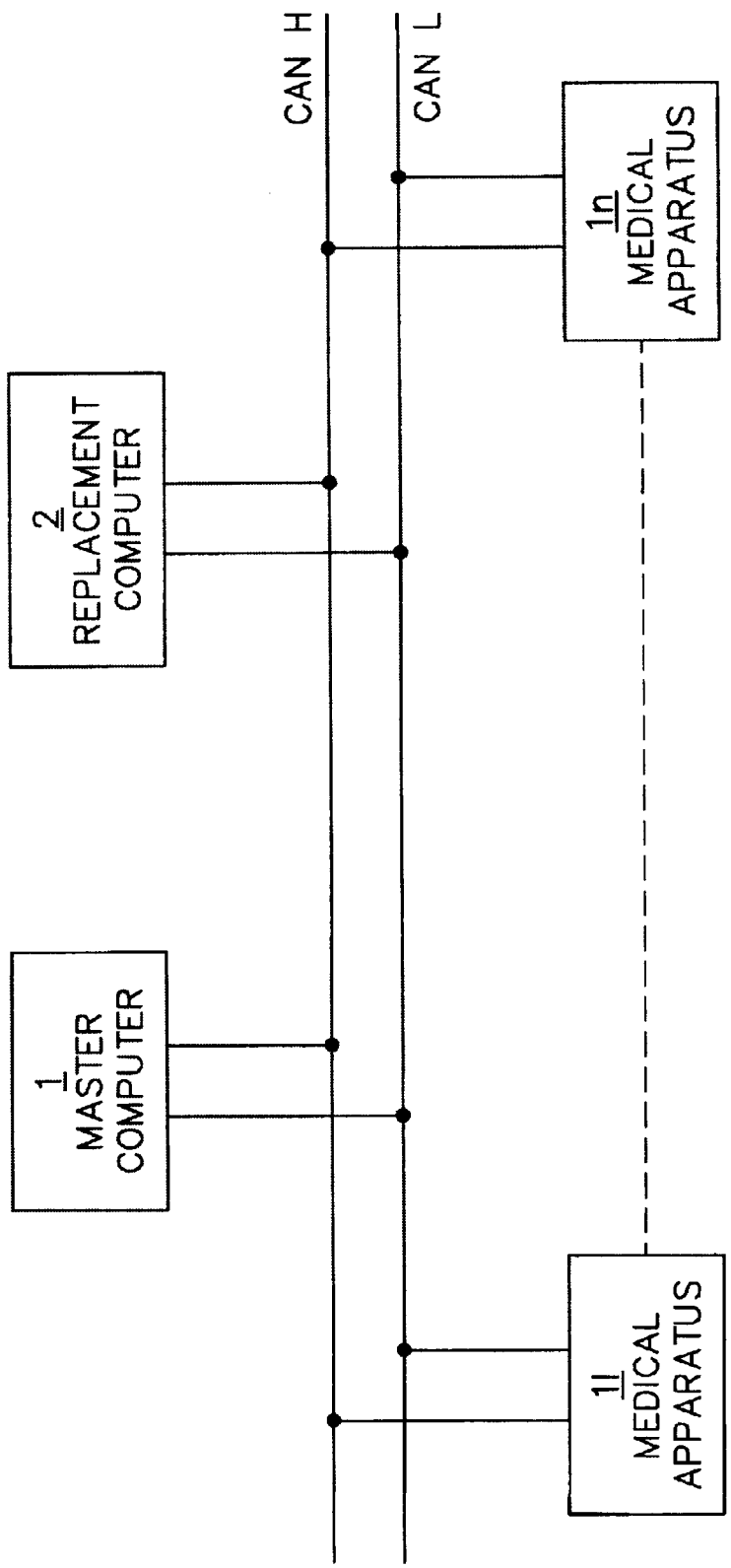

Fig. 2A

Figure 2B:
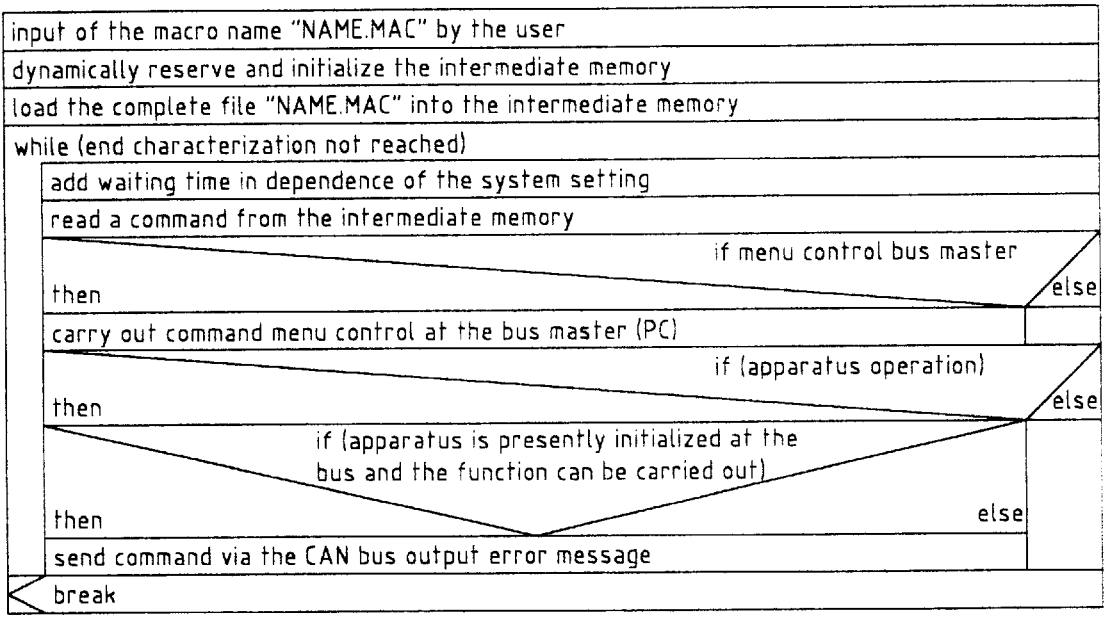

```
while (macro-recorder "RECORD" activates)
    dynamically reserve and initialize intermediate memory
                                    if menu control at the bus master (PC) is actuated
                                                              via voice control/joystick
    then                                                                              else
    deposit memory control demands in the intermediate memory
                                    if apparatus operation at the bus master (PC) is actuated
                                                              via voice control/joystick
    then                                                                              else
    deposit system operation in the intermediate memory
                                    if (apparatus operation is carried out at the apparatus)
    then                                                                              else
    deposit apparatus operation in the intermediate memory
carry out end characterization of the macro
input of the macro name "NAME.MAC" by the user
storage of the complete intermediate memory in a non-volatile memory
(e.g. hard disk, EEPROM, etc) under the name "NAME.MAC"
    break
```

DEVICE AND A METHOD FOR THE AUTOMATIC CONTROL AND ADMINISTRATION OF MEDICAL APPARATUS AND INSTALLATIONS

The invention relates to a method and a device for the automatic control and administration of program-controlled medical apparatus or installations, in particular of endoscopic apparatus, according to the features specified in the preamble of the claims 1 and 9.

The administration, system setting and configuration of various medical apparatus used in an operation and in particular endoscopic apparatus must presently, before each operation, still be carried out manually by the operating personnel. For various operations or with various operation techniques for this various apparatus must each time be completely reset. Also the administration of apparatus or apparatus parts which are defect or are to be routinely exchanged is presently protocolled and monitored by hand.

If with known endoscopic systems technical problems occur shortly before or during the operation then presently the complete handling must still be carried out by the operating personnel. On account of the fact that here it is a case of highly complex systems with which often several electronic apparatus and instruments must cooperate in the most varied of configurations, the operating personnel is often not informed in detail of the very extensive measures and possibilities with the occurrence of a particular error or problem.

To make matters difficult with this there is added the stress of the operating personnel as well as the time problem with regard to overcoming the problem or error during the operation. Also technically orientated users often may not, or only insufficiently acquire and localize the corresponding problematics on recognizing an error or problem.

DE 693 15 961 T1 is concerned with a known device and a method by way of which, by way of a non-volatile memory which is provided in a peripheral apparatus (printer) connected by a LAN to other intelligent apparatus and is provided on a circuit board which furthermore comprises a bi-directional interface for coupling the circuit board to the peripheral apparatus and a LAN interface arranged on the circuit board, for coupling the circuit board to the LAN as well as a processor, resets the peripheral apparatus (the printer) after the use into a known configuration which is the same for all users. With this for each user the same apparatus data and settings are fixed.

U.S. Pat. No. 5,812,397 describes a communication via a serial interface which is to be seen as a standard interface. Theoretically this communication in order to make it more secure and quicker may also be controlled via a CAN bus. U.S. Pat. No. 5,812,397 however at no location mentions a CANopen communication protocol or an extended CANopen structure which could permit a communication with equality of access, between in each case two slave units.

DE 197 22 221 A1 describes only a physical connection of CAN slaves to the CAN master. This means that this document discloses the standard of the CANopen bus. DE 197 22 221 A1 however does not give any hint how the number of slave-to-slave communication possibilities may be increased.

As is known the CAN bus structure, e.g. in the automobile industry, is used for the application in the motor vehicle, since the great and numerous malfunctionings occurring here are mastered very well with the CAN bus.

It is the object of the invention to provide a method and a device for the automatic administration of apparatus and installations which are spatially and functionally allocated to one another, in particular of endoscopic apparatus, which relieve the personnel and may save costs for the administration and/or the setting of the apparatus.

The part of the object with respect to the method is achieved by the features specified in claim 14, the part with respect to the device by the features specified in claim 22.

The method and the device are in the position of simultaneously controlling or monitoring the apparatus or installations of several operating theaters or operations.

The method according to the invention and the device bring a considerable simplification of the system operation for the operating personnel, since before a certain operation all apparatus, in particular of an endoscopic system, may be brought into the configuration and apparatus setting necessary for an operation or operation technique.

Furthermore according to the invention all changes or settings which during an operation are carried out on the apparatus, may be automatically acquired. In particular a multitude of operating steps which are necessary before an operation on all apparatus required for an operation may be reduced to a single system operation. Every surgeon employed with the operation may with this take into account his subjective demands with the system setting and simultaneously with the beginning of the operation may be sure that for each particular application his defined system setting has been carried out.

So that the long term absence of breakdown of a complete system may be extended and in order to save maintenance costs the user is in good time made aware, by way of suitable messages on the monitor of a master computer or of another output apparatus, of critical installation components, such as the exchange of wearing parts, the refilling of fluids and gas, electronic or physical problems, and is also made conscious of the suitable point in time for the maintenance of the installation or of individual apparatus. By way of this the probability of the arising of a system error, apparatus error or breakdown during operation is significantly reduced.

Furthermore according to the invention it is possible to understand all information arising with a medical instrument or endoscopic system during an operation, also afterwards. Furthermore such information may be sent for documentation purposes, i.e. be stored.

The operating personnel are relieved above all with technical problems occurring during an operation, since on recognition of a system disturbance, of an apparatus error or a breakdown of this, in the whole system there is effected a suitable intelligent treatment of the situation. With this the actual system condition is automatically acquired and analyzed. Subsequently according to possibility the corresponding error elimination, such as e.g. the replacement of a broken down apparatus by a similar one, is initiated automatically.

For fulfilling the above mentioned objects the apparatus of one or more operating theaters of a clinic are connected to one another and to a master computer by way of a CAN bus with an opened CANopen structure, by way of which they may be centrally administrated or controlled.

All apparatus according to the invention have at their disposal an intelligent program-controlled processor unit and are in the position, via the CAN bus, of informing all occurring process data or parameters to one another and to the master computer.

By way of special control, administration, communication and error protocols defined for each of the connected-up apparatus and for the master computer all the above mentioned objects may be realized with respect to software. The software is implemented in the whole system, i.e. in the master computer and in the connected-up apparatus.

The communication is effected by changing the standardized CANopen protocol. This uses standard point-to-point connections (peer-to-peer connections). By changing the communication structure logical transmitting and receiving addresses as well as hardware transmitting and receiving buffers are saved. These apparatus communicate with the opened CANopen master slave protocol either via a double ring structure, a ring-star structure or a ring-ring structure. These communication structures are however not made possible with respect to hardware but logically via a suitable addressing.

With the double ring structure if the number of nodes remains equal the transmission time is shortened and the bus load is reduced, since the communication takes place in two directions. For each node, i.e. the interface of an apparatus, of the master computer and of the replacement computer, the node IDs of all other nodes accommodated in the ring must be known by way of an algorithm, by way of address lists or by way of transmission from the master computer. The nodes then decide which path is the shortest transmission path.

With a ring-star structure star outer points are connected to one another by a ring structure. Apparatus which belong to a system or to a group of apparatus and thus require a fast data exchange are connected together to a star. In this case there takes place a peer-to peer connection between the star point and the star outer point as the quickest transmission form. The communication between star outer point and star outer point takes place via the star point (star outer point->star point->star outer point).

For each node the node IDs of all other nodes accommodated in the ring must be known via an algorithm or via address lists or by way of transmission from the master computer.

The node IDs are present for the nodes in a table/matrix. From the table the node IDs of a line are grouped together to a star. According to an algorithm a star point is selected. The star points of all lines of the table are connected to one another via a ring structure.

With the ring-ring structure those participants which relatively often exchange data with one another are connected together to a ring. If further participants are at the bus also these are configured to a further ring. The configuration of a ring is effected as with the configuration of a ring with the double-ring configuration.

In order to permit the communication between all medical apparatus certain nodes of the respective rings are connected together to a common ring. This is carried out equivalently to the method of the connecting together of the star points to a ring with the ring-star structure.

Figure 2C:
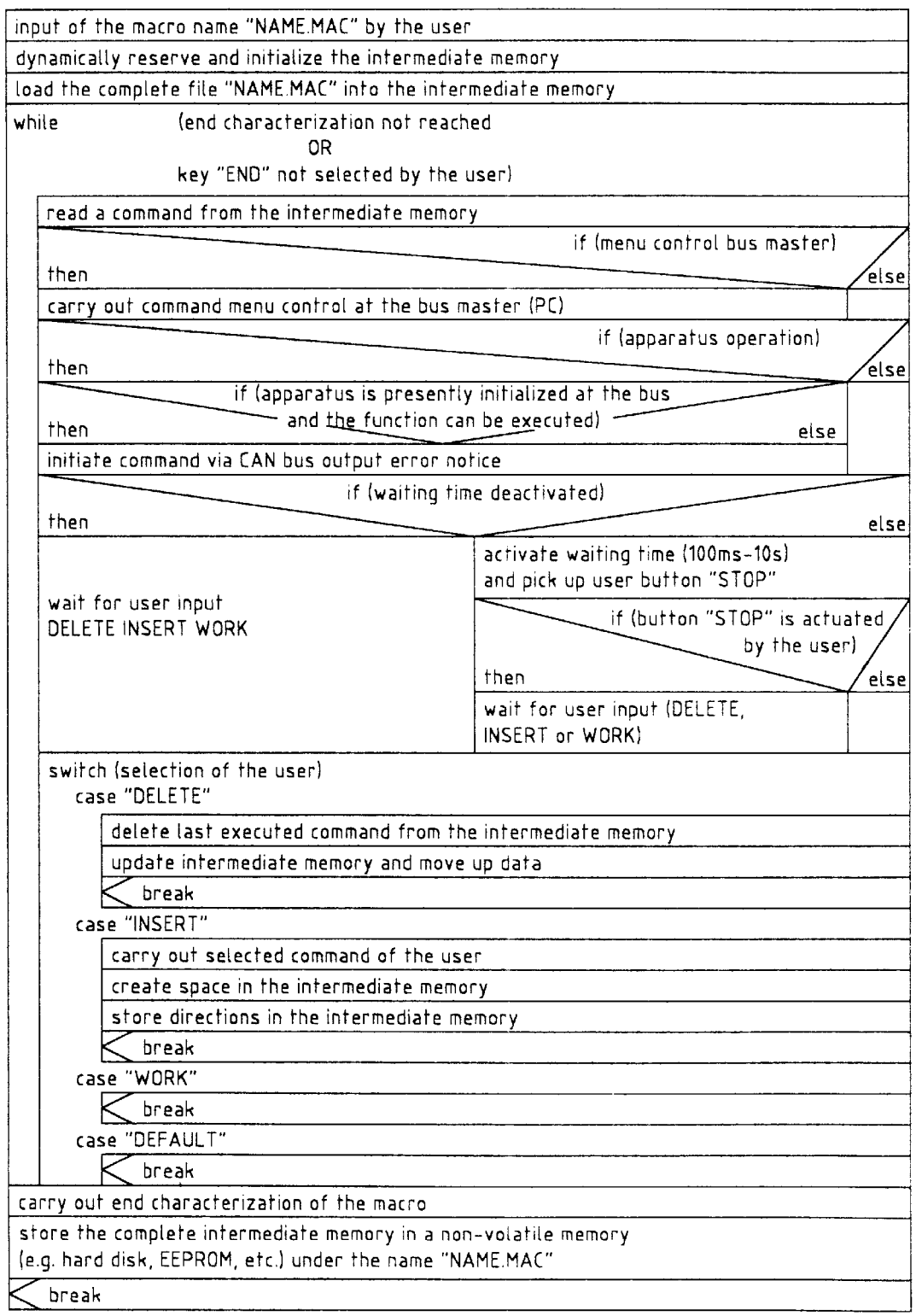
Figure 3:
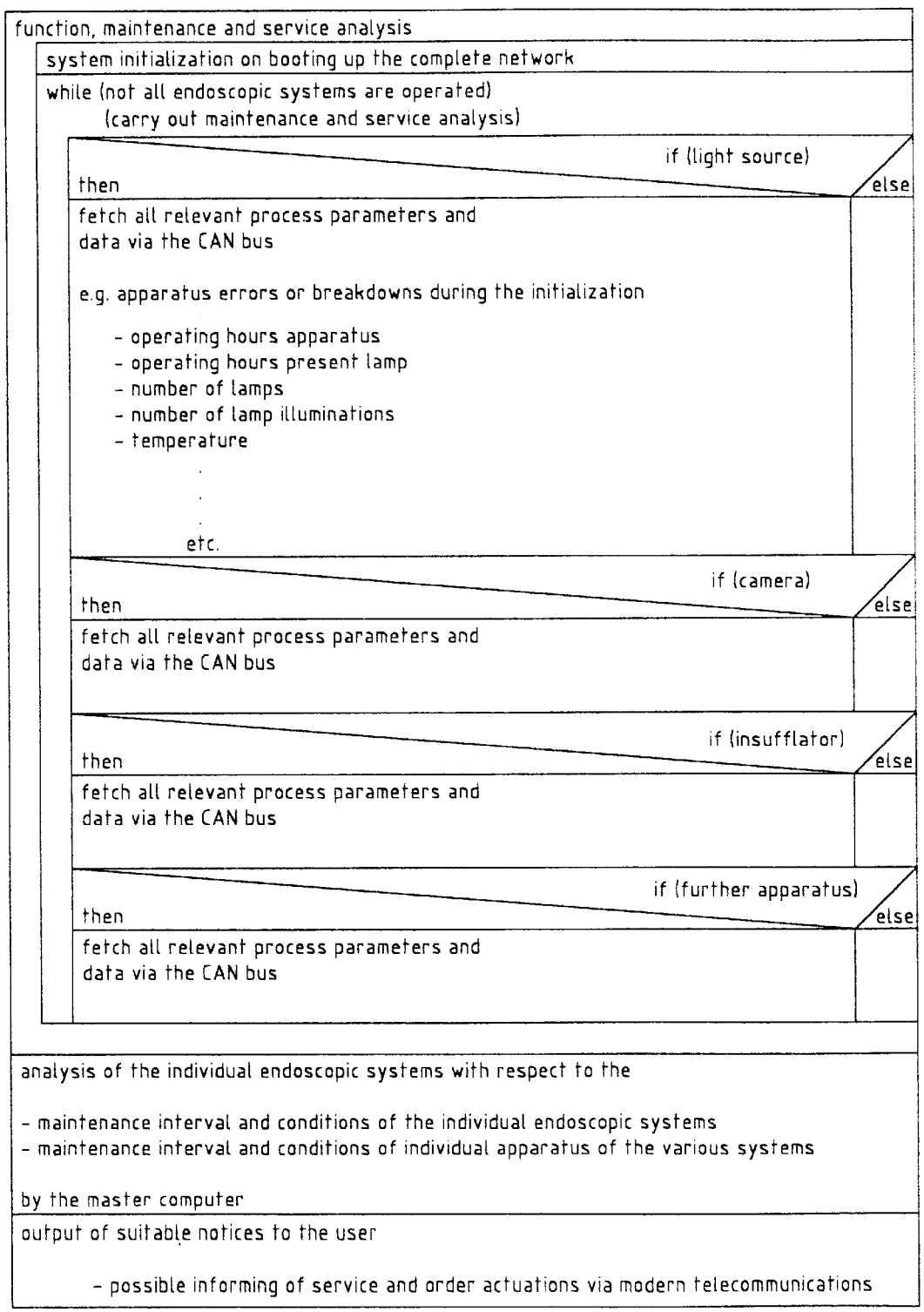
Figure 4:
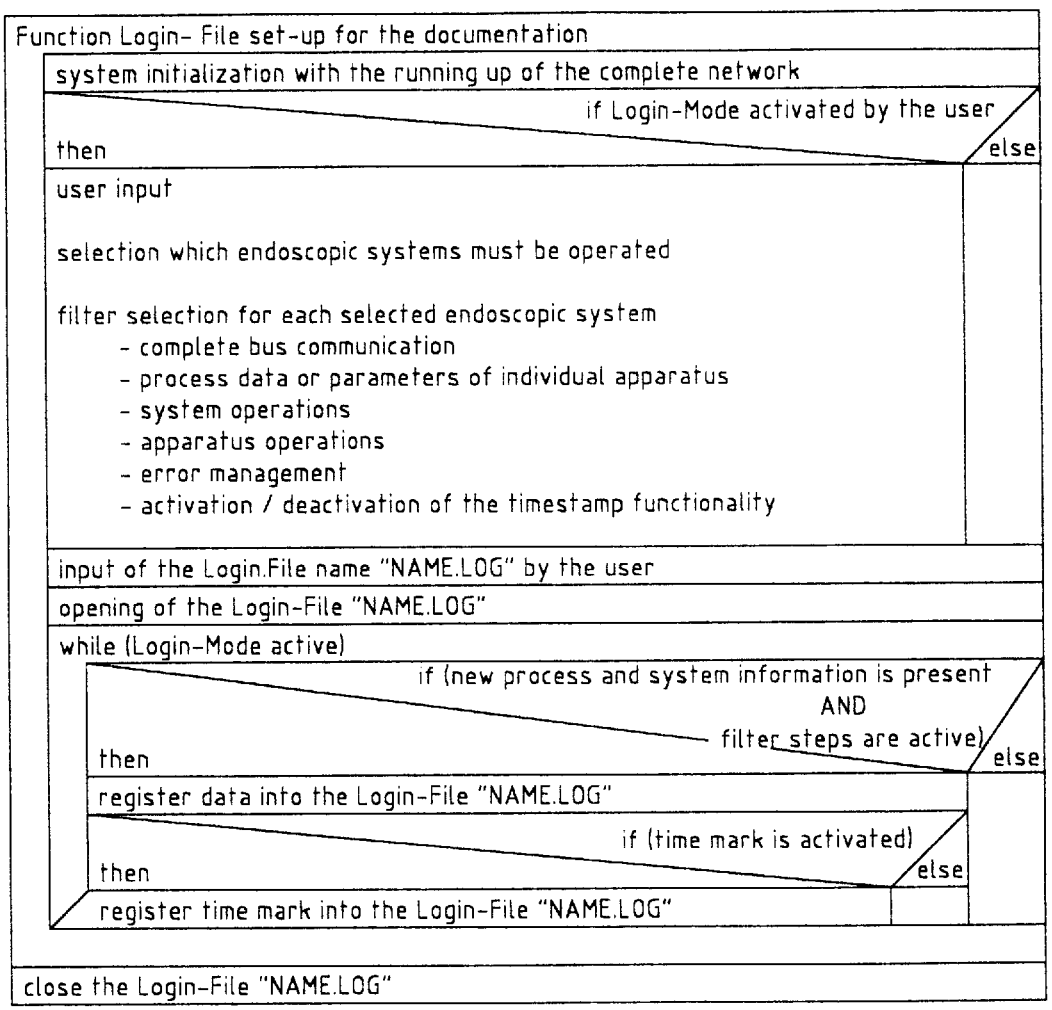
Figure 5:
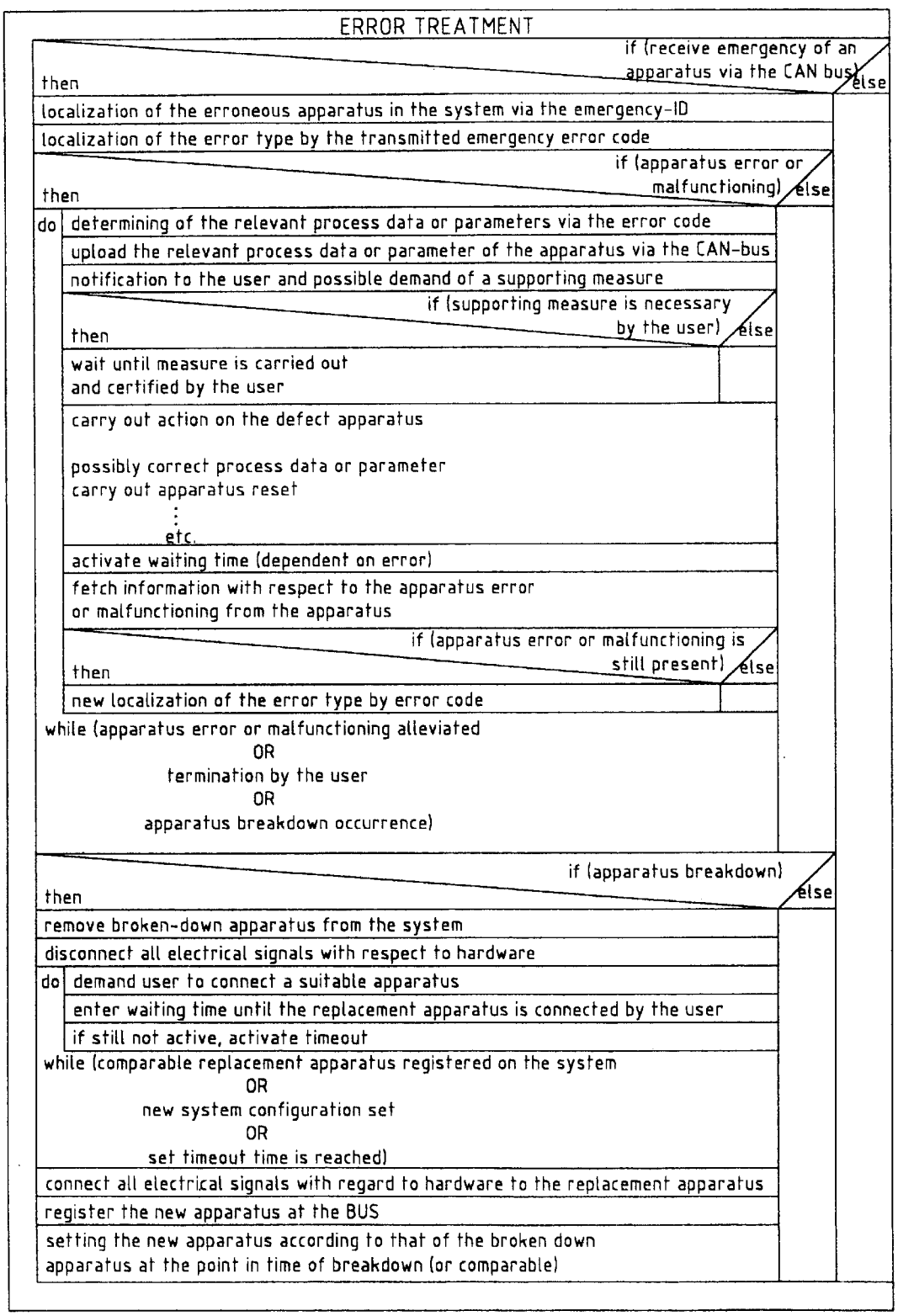
Figure 6A:
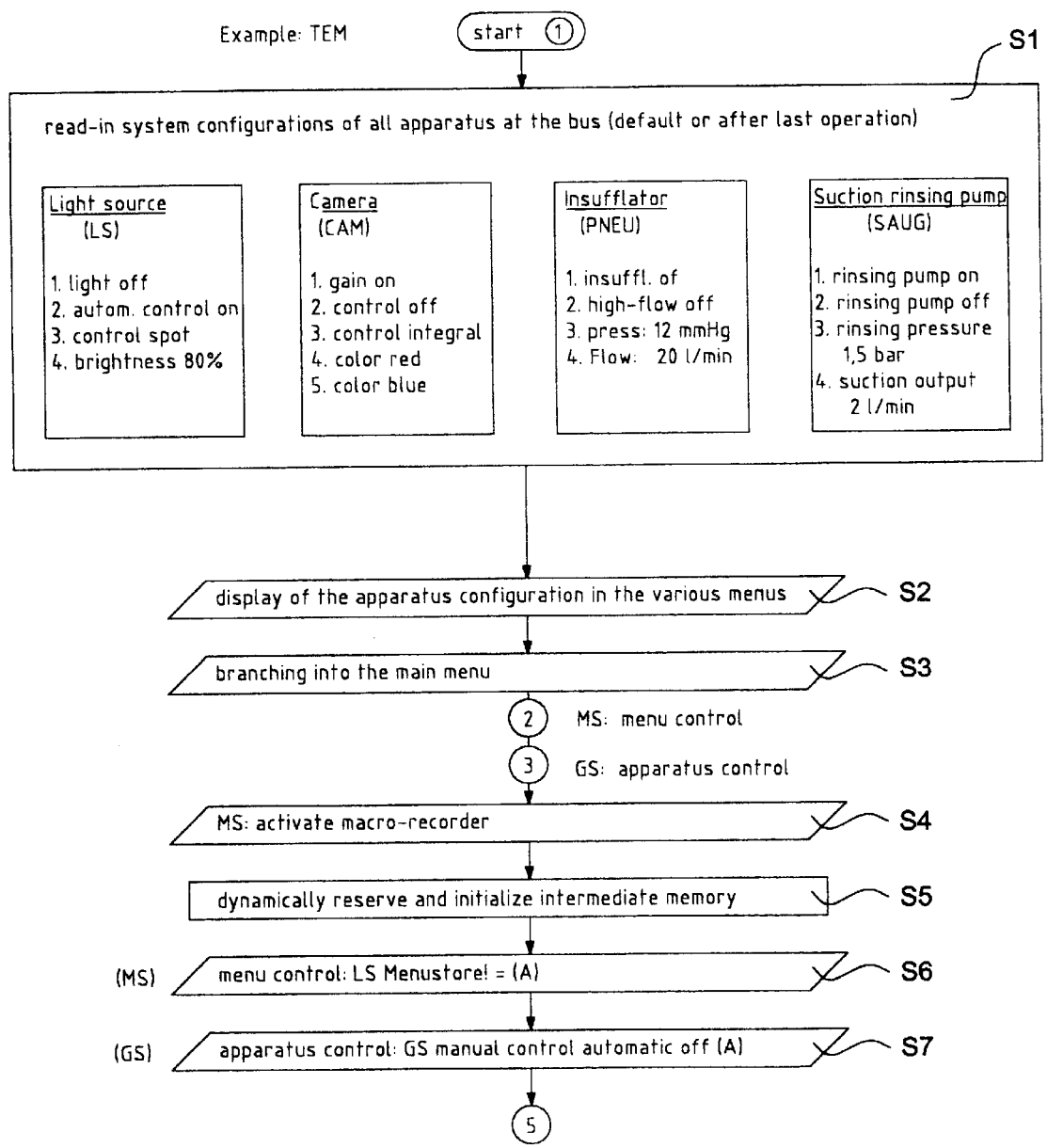
Figure 6B:
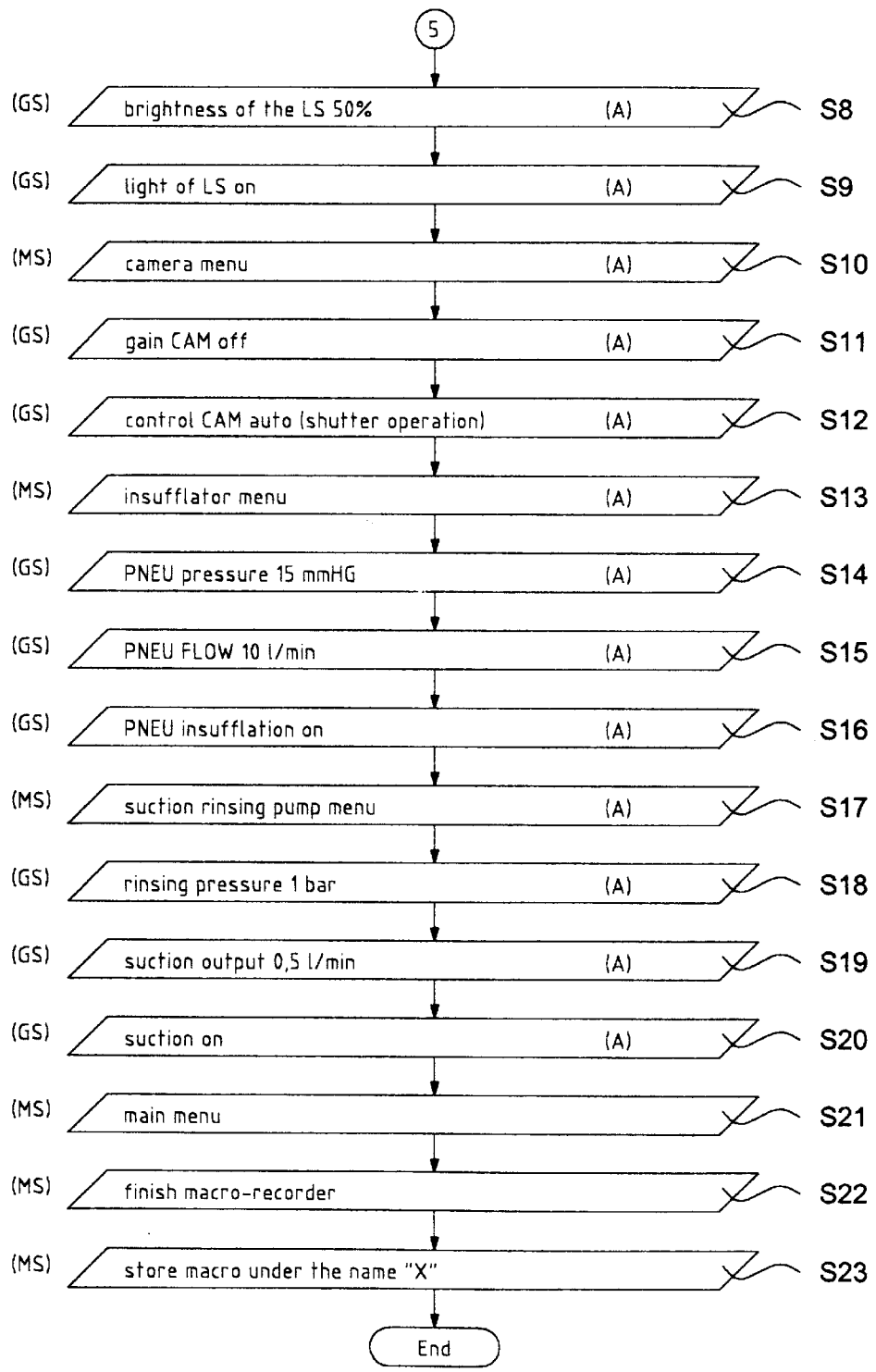
Figure 7:
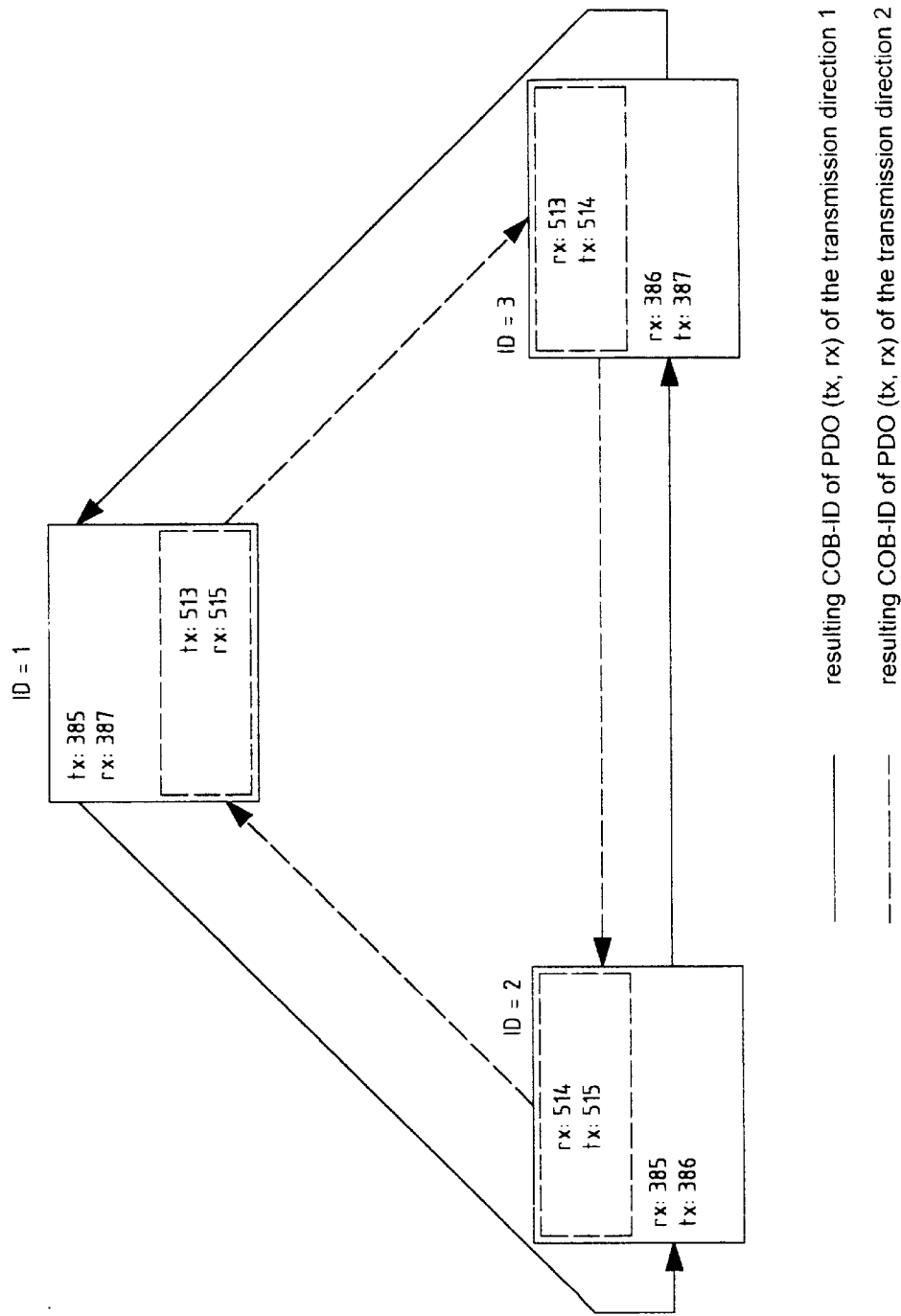
Figure 8:
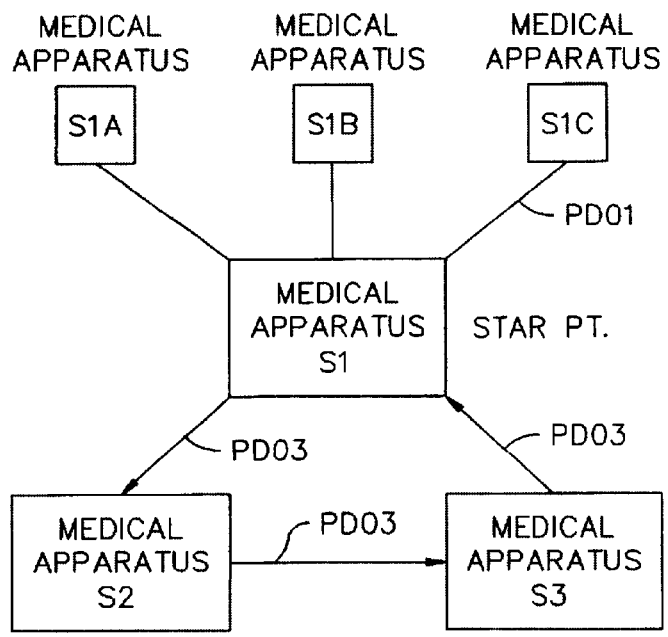

The invention is hereinafter described in more detail by way of embodiments described in the drawings. There are shown:

FIG. 1 a block diagram of a system of several medical apparatus or installations, a master computer and a replacement computer, the system being suitable for carrying out the method according to the invention and being connected by a CAN-bus;

FIG. 2A a schematic procedural diagram of a software-macrorecorder used with the method according to the invention, for drawing up and storing a macro;

FIG. 2B a schematic procedural diagram for loading and playing a macro into the system;

FIG. 2C a schematic procedural diagram of a program serving the loading, playing, changing and storing a macro;

FIG. 3 a schematic procedural diagram of a program serving the maintenance and service analysis;

FIG. 4 a schematic procedural diagram of a LOG-IN-FILE setting-up for documentation;

FIG. 5 a schematic procedural diagram of a program serving the error treatment in the device according to the invention;

FIGS. 6A and 6B an example of a macrorecorder for a system of endoscopy apparatus consisting of a camera, light projector, insulator and suction rinsing pump;

FIG. 7 schematically a double ring structure;

FIG. 8 schematically a ring-star structure and

Figure 9:
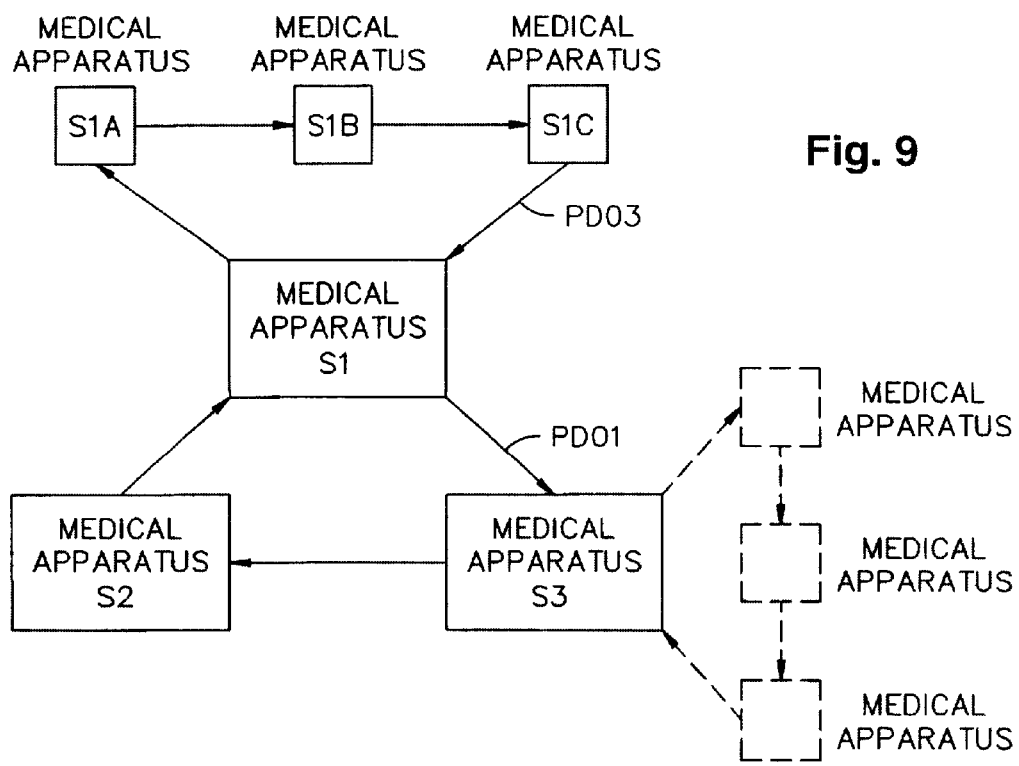

FIG. 9 schematically a ring-ring structure of several apparatus connected by a CAN-BUS.

The block diagram shown in FIG. 1 schematically shows several medical apparatus $1l$–$1n$, which may be endoscopy apparatus which are connected to one another via a CAN-bus and are connected to a higher order master computer 1 and to a replacement computer 2. Via the bus leads CAN_H and CAN_I CAN-bus or data telegrams are transmitted bidirectionally. With this, according to the invention also a communication with equality of access and thus a fast communication of the medical apparatus $1l$–$1n$, connected to one another by the CAN-bus, amongst one another is possible.

In one example the apparatus $1l$–$1n$ may comprise a light projector, a video camera, an insufflator, a suction rinsing pump etc. and may be operated by the central control unit described as a master computer. These apparatus are administrated by the master computer 1 e.g. as a first apparatus group A, which e.g. belongs to an endoscopic system of an operating theater of a clinic. As mentioned also a quick data exchange between the apparatus of the light projector, camera, insufflator, suction rinsing pump is possible. Thus the camera for example may transmit control values (video signal) via the bus to the light projector. Likewise the insufflator may transmit data for blending in text on the monitor via the CAN-bus to the camera.

A second apparatus group B under the apparatus $1l$–$1n$ consists e.g. of a light projector, a camera and an insufflator and of a suction rinsing pump which belong to another endoscopic system of another operating theater of the same clinic. Also with this group of apparatus a quick data exchange of the apparatus amongst one another is necessary via the CAN-bus.

Since all apparatus groups by way of the CAN bus by way of the opened CANopen protocol communicate with one another and with the higher order master computer or in the case of an error in which the master computer 1 malfunctions—with the replacement computer 2, a real time data exchange between the individual apparatus as well as between the apparatus groups is possible. With this the time delay is reduced in comparison to known structures where settings parameter changes, maintenance measures, error notices must be carried out and protocolled separately on the individual apparatus.

As will be described in more detail further below the bus structure of the CAN bus is principally based on the layer-7-protocol which is however opened so that by way of the addressing, logically several different communication structures e.g. a double ring structure, a ring-star structure and a ring-ring structure may be realized with the same CAN bus.

On the basis of the hardware structure represented schematically in FIG. 1 as a block diagram, now by way of the procedural diagrams represented in the FIGS. 2A, 2B, 2C and 3 to 5 an intelligent system management is described, which consists of the following parts:

1. macro-recorder (FIGS. 2A, 2B, 2C);
2. maintenance and service analysis according to FIG. 3;
3. LOG-IN-FILE setting-up for documentation according to FIG. 4 and
4. error treatment according to FIG. 5.

1. Macro-recorder (FIGS. 2A. 2B, 2C)

Via the macro-recorder the user of endoscopic systems may put together and store the complete system setting for certain operation types and operation techniques in a one-off procedure.

The macro-recorder may at the same time be activated (FIG. 2A) by the user of a endoscopic system completely initialized by the master computer. Thereafter all made adjustments on all apparatus of the system or on the master computer 1 are drawn up. After deactivation of the macro-recorder a macro-file co-protocolled by the master computer is saved in a present data memory under a name which is inputted by the user.

By calling up the macro-recorder and the inputting of the file name of the corresponding macro-file this may be played into the system (FIG. 2B). The endoscopic system is then configured in exactly the way and manner as this is described in the corresponding macro-file.

The macro-recorder is not bound by the master computer 1, i.e. the necessary software may also be implemented into an apparatus in order only to configure this one apparatus. The configuration of the apparatus may also be effected via suitably programmed chip cards which are introduced on the corresponding apparatus.

Apart from the functions RECORD and PLAY of the macrorecorder, via the function CHANGE the already stored macro may be changed without problem (FIG. 2C).

2. Maintenance and Service Analysis after Booting Up the System (Boot-up)

After the "boot-up" of the endoscopic system all process data and process parameters with respect to the system upkeeping or the apparatus maintenance (condition of apparatus parts, auxiliary means, etc) of all endoscopic apparatus of the system are read in by the master computer. By way of this data the master computer is set in the position of completely analyzing the condition of the system and informing the user via the monitor of measures with respect to maintenance or an exchange of wearing parts or of necessary auxiliary means.

3. LOG-IN-FILE Setting Up for Documentation (FIG. 4)

Usually the master computer only monitors and processes the information of the bus system which is important for it. Via a LOG-IN-MODE the whole bus communication of a clinic may be provided with time markers by the master computer and co-protocolled and stored in a LOG-IN-FILE.

Which data with this are deposited in the LOG-IN-FILE may be set by the user on the master computer via filters. With this the protocolling may be selected under the following possibilities:

complete bus communication
data of individual operations
data of individual apparatus
system or apparatus operations
all/certain process parameters or process data
error treatment By way of the marking of the whole communication documentation via time markers in the LOG-IN-FILE also retrospectively the detailed course, with respect to time, of the drawn-up communication in all operations may be understood.

4. Error Treatment (FIG. 5)

With an apparatus error or an apparatus malfunction according to possibility the error is automatically corrected. With this the process data responsible for the problem are read into the master computer 1 by the respective unit. This master computer then decides by way of a matrix, whether this problem may be corrected immediately (immediate execution!) or whether a supported measure by the user is necessary (output on the monitor/apparatus), before an error correction may be initiated.

If it is the case of an apparatus breakdown or of a great malfunction which cannot be corrected in a defined temporally tightly limited period of time, then the corresponding apparatus is removed from the system by the master computer. With this the apparatus is de-registered from the system via the bus. Furthermore all relevant electrical signals are connected away from the system via electronics set up for this.

A present replacement apparatus is then automatically incorporated into the system by the master computer. The relevant electronic signals are then switched onto the new apparatus. The configuration of the new apparatus is then carried out corresponding to that of the defect apparatus at the point in time of breakdown. If both apparatus are not directly comparable then the best possible setting for the application in hand is automatically selected by the master computer. The operation may be continued directly after this automatized measure.

Via the error treatment the master computer 1 is monitored by a replacement computer 2. This likewise co-protocols the whole bus communication and is thus in the position, with a possible breakdown or system failure of the master computer 1, to maintain the function of the CAN-bus. This object is realized from the software side up to the hardware necessary for the re-connection.

On storing the data in the LOG-IN file the data traffic of all apparatus in the system is protocolled. The data of the LOG-IN file may be prepared, filtered and thus evaluated according to the respective demands after the operation. With this with a later evaluation the data is available in a temporal grid in which they occur with the drawing-up. With errors which occur with the apparatus operation or with the apparatus, it may therefore be exactly ascertained which bus telegrams or which apparatus operation settings are present or carried out at the point in time of the error. Thus errors may be exactly traced. The error treatment is by way of this decisively improved. If the LOG-IN file is run off or played all settings carried out during the operation, i.e. settings which were carried out on an operating panel of an apparatus as well as settings which were carried out via the bus-master, or the master computer, are again carried out on the apparatus. Thus each operation may be exactly analyzed.

As an example of data acquired by endoscopic apparatus there are mentioned operating data, such as flow value, pressure (in each case nominal and actual value), suction output, brightness value, gas temperature in dependence on the flow rate, etc. Other data which are to be acquired are e.g. error notices.

Now by way of the FIGS. 6A and 6B there is described an example for a macro-recorder in a system which consists of the following endoscopy apparatus: camera, light projector, insufflator, suction rinsing pump.

Firstly the start configuration of all apparatus connected to the system is recorded (step S1). This is effected per "default". The configurations of the apparatus light projector (LS), the camera (CAM), insufflator (PNEU) and suction-rinsing pump (SAUG) commanded in step S1 is only an example for transanal endoscopic microsurgery.

By way of step S2 the apparatus configuration recorded in step S1 is displayed in the various menus. One then branches into the main menu (S3) and in step S4 the macro-recorder is activated. Here and in the following there applies the following:

MS—"menu control"
GS—"apparatus control"
A—"storage"

In step S5 dynamic intermediate storage space is reserved and initialized. Then in step S7 the light source menu is called up, and the values are stored; in step S7 the manual apparatus control is selected, i.e. that the automatic control is switched off. The selected parameter "manual" is stored. In step S8 the brightness of the light source LS is set to 50% and in step S9 the light source is switched on. The brightness value of step S8 and the switching-on in step S9 are both stored. Then in step S10 the camera menu is called up and stored. The gain of the camera CAM is switched off in step S11 and this step is stored. Then in step S12 the control of the camera CAM is set to automatic, i.e. shutter operation and this setting is stored. In step S13 by way of the menu control the insufflator menu is called up and stored. The pressure of the insulator (PNEU) in step S14 is set to 15 mm Hg and this pressure value is stored. In step S15 the flow rate of the insufflator is set to ten liters per minute and this flow rate is stored. Then the insulator is switched on and this procedure is stored (step S16).

Subsequently in step S17 the suction-rinsing pump menu is selected and this procedure is stored. In step S18 the rinsing pressure of the suction rinsing pump is set to one bar and this pressure value is stored. In step S19 the suction output is set to 0.5 l/min and stored. In step S20 the suctioning is switched on and this activity is stored. One then branches into the main menu (step S21) and in step S22 the macro-recorder is finished and finally is stored under a name "X" in step S23.

Hereinafter by way of the FIGS. 7 to 9 mixed bus structures for optimizing the communication of the medical apparatus connected to one another by the CAN bus, in particular endoscopic apparatus, with an opened CAN open communication, is described in more detail.

CANopen is a protocol which is based on communication objects (COB), wherein to each communication object there is allocated an identification, which implicitly specifies its priority. The allocation of the identification to the COBs is an essential factor of the system design.

The communication object identifications (COB-IDs) and the holding times may be distributed to the apparatus either statically or dynamically. "Static distribution" means that object identifications and holding times are fixed and may only be changed by way of a respective module or apparatus or individual means such as e.g. switches and adaptation software. In contrast a "dynamic distribution" means that the identification and the holding times are distributed over the CAN bus by way of standardized services and protocols. Some identifications (1 to 2, 1740–1769 DEC) are reserved by the CANopen.

With the applied layer-seven protocol CANopen the communication is effected with a process data object (PDO). The PDO is a CANopen telegram. For the master-slave communication there are available two PDOs.

According to the invention the slave communicates with the master, i.e. with the master computer, further via the CANopen telegram PDO2. A date with PDO2 (tx) is sent by the master, e.g. by the master computer and received by the slave with PDO2 (rx). The slave-slave communication is realized by opening the standard CANopen master-slave structure in the following manner:

a) Double Ring Structure (FIG. 7)

With a simple ring, information would be received by the previous node and transmitted to the next node. The communication would only be possible in one direction. By way of the further reaching of an information there arises a time delay. The maximum number of participators in the ring may be computed from the maximum allowable delay time.

By way of the introduction of a second ring a communication in both directions is possible. The maximum number of participants doubles, since the communication takes place in two directions. With an equal remaining number of nodes the transmission time is shortened and the bus load is reduced, since the communication is effected in two directions. For each node the node-IDs of all other nodes accommodated in the ring must be known via an algorithm, via lists or by way of transmission from the master. The nodes thereon decide which path is the shorter communication path.

Formation of ring 1:
COB-ID of PDO1(tx)=384+node-ID (node)
COB-ID of PDO1(rx)=384+node-ID (previous node in ring)
Formation of ring 2:
COB-ID of PDO3(tx)=512+node-ID (node)
COB-ID of PDO3(rx)=512+node-ID (next node in ring)
or
Formation of ring 1:
COB-ID of PDO1(tx)=512+node-ID (node)
COB-ID of PDO1(rx)=512+node-ID (previous node in ring)
Formation of ring 2:
COB-ID of PDO3(tx)=384+node-ID (node)
COB-ID of PDO3(rx)=384+node-ID (next node in ring)
The rx/tx-COB-ID of the nth/(n-1)th node in the ring is always the tx/rx-COB-ID of the (n-1)th/nth node in the ring.

The node-IDs of all nodes participating in the double ring are present at each node according to an algorithm or according to a list or by way of transmission by the bus-master.

Example

| Node: | A | B | C | D | E | F |
|---|---|---|---|---|---|---|
| Node ID | 1 | 2 | 3 | 4 | 5 | 6 |
| COB-ID of PDO1 (tx) | 385 | 386 | 387 | 388 | 389 | 390 |
| COB-ID of PDO1 (rx) | 390 | 385 | 386 | 387 | 388 | 389 |
| COB-ID of PDO3 (tx) | 513 | 514 | 515 | 516 | 517 | 518 |
| COB-ID of PDO3 (rx) | 514 | 515 | 516 | 517 | 518 | 513 |

A transmission from node D to node B is to be effected. The transmission is possible in the sequence D, E, F, A, B as well as in the sequence D, C, B. Node D decides on the shorter path D, C, B.

b) Ring-star Structure (FIG. 8)

With a ring-star structure star transmission shapes are constructed in which certain nodes configure as a star point or are configured by the master as a star point. Nodes are grouped together to a star which relatively often exchange data with one another per unit of time. The star point with this passes through data from the nodes connected to the star point. With a star a date thus at the most must be passed through once. This permits a quick communication. The node which transmits the most data per unit of time in sensibly the star point. Thus a peer-to-peer communication takes place, thus the quickest transmission form.

In order to permit a communication with further endoscopic apparatus the star points are connected to one another via a ring structure. For each node the node-IDs of all other nodes accommodated in the ring must be known via an algorithm or via lists or by way of transmission from the master. The node IDs are present at the nodes in a table/matrix. From the table the node-IDs of a line are grouped together to a star. According to an algorithm a star point is selected. The star points of all times of the table are connected to one another by a ring structure.

Formation of a star:

Star point:

COB-ID of PDO1(tx)=384+node-ID (star point)

COB-ID of PDO1(rx)=(512+node-ID (node A)) AND (512+node-ID(node B)) . . .

PDO1(rx) is received in the BasicCAN-message-object. The mask is set to

MASK=(512+node-ID (node A)) EQUIVALENCE (512+node-ID (node B)) . . .

With this 2^(number of nodes at the star point) information must be filtered out.

Participants connected at the star point:

COB-ID of PDO1(tx)=512+node-ID (node x)

COB-ID of PSO1(rx)=384+node-ID (node x)

Formation of a ring:

COB-ID of PDO3(tx)=896+node-ID (node)

COB-ID of PDO3(rx)=896+node-ID (next node in ring)

The rx/tx-COB-ID of the nth/(n−1)th node in the ring is always the tx/rx-COB-ID of the (n−1)th/nth node in the ring.

Example

A node is the star point (here: nodes A1, e.g.: light projector)

| node A1 | node B1 | node C1 | node D1 | node E1 |
|---------|---------|---------|---------|---------|

PDO1(tx)→PDO1(rx)

PDO1(tx)→PDO1(rx)

PDO1(tx)→PDO1(rx)

PDO1(tx)→PDO1(rx)

PDO1(rx)←PDO1(tx)

PDO1(rx)←PDO1(tx)

PDO1(rx)←PDO1(tx)

PDO1(rx)←PDO1(tx)

Node A1 is e.g. star point 1, node A2 is the star point 2, etc.

| node A1 | node A2 | node A3 | node A4 |
|---------|---------|---------|---------|

PDO3(tx)→PDO3(rx) PDO3(tx)→PDO3(rx)

PDO3(tx) PDO3(tx)→PDO3(rx) PDO3(tx)→ c) Ring-ring Structure (FIG. 9)

With a ring-ring structure several ring systems are combined with one another. With a ring, information is received from the previous node and sent to the next node. By way of passing further information there arises a time delay. The maximum number of participants may be computed from the maximum allowable delay time. In order to keep the maximum delay time as low as possible only relatively small rings are configured. With this 3 to 8 participants are sensible. With this the participants which relatively often exchange data with one another are connected together to a ring. If there are further participants at the bus, these participants are configured to a further ring. The configuration of a ring is carried out as described in a) (ring 1).

In order to permit the communication between all medical apparatus certain nodes of the respective rings are connected together to a ring. This is carried out equivalent to b) (connecting together the star points to a ring).

What is claimed is:

1. A method for automatically controlling and administering one or more program-controlled endoscopic apparatuses, within one or more operating theaters belonging to a clinic region, the method comprising:

(a) connecting the apparatuses among one another and to a higher order master computer using a CAN-bus having a CANopen structure, the CAN-bus enabling equal access communication between each of the apparatuses and the master computer;

(b) providing software interfaces in the apparatuses and the master computer connected to the CAN-bus, the interfaces defining CANopen control, administration, communication and error protocols for each of the apparatuses and the master computer;

(c) generating macros describing a system configuration, the macros adhering to the protocols defined in step (b);

(d) setting process parameters for at least one of the apparatuses by transmitting at least one of the macros to at least one of the apparatuses;

(e) reporting the process parameters and error conditions of at least one of the apparatuses to the master computer;

(f) recording data content of the at least one the macros transmitted in step (d) and of the process parameters reported to the master computer in step (e); and (g) repeating steps (c)–(f) for each setting change of at least one of the apparatuses.

2. The method of claim 1, wherein the process parameters for multiple apparatuses are set in a single operation step.

3. The method of claim 1, wherein step (e) includes transmitting process data and process parameters regarding service and maintenance of the apparatuses connected to the CAN-bus to the master computer.

4. The method of claim 1, wherein during steps (d)–(f), the master computer assigns time markers to the communication on the CAN-bus and records the communication with the time markers in a documentation file.

5. The method of claim 4, wherein a user selects data filters for determining which communication is recorded in the documentation file, the data filters selected from a group including complete bus communication, individual operating theater data, individual apparatus data, system or apparatus operations, selected process parameters or process data and error treatment.

6. The method of claim 1, further comprising:
   (h) transmitting process data regarding an error to the master computer, wherein using a decision matrix the master computer determines if the error is alleviated immediately or whether a supporting measure by the user is necessary, and
   (i) displaying a decision result on a display unit of the master computer or one of the apparatuses prior to alleviating the error.

7. The method of claim 6, wherein upon replacement of a defective apparatus, the master computer configures a replacement apparatus identical to the defective apparatus according to the setting of the defective apparatus at the time of breakdown.

8. The method of claim 1, further comprising:
   (i) monitoring the master computer with a replacement computer, wherein the replacement computer co-protocols the communication on the CAN-bus and maintains functionality of the CAN-bus upon breakdown or error of the master computer.

9. A device for carrying out the method of claim 1, wherein each of the apparatuses and the master computer comprise a CAN-bus interface, and the communication protocol of the CANopen structure allows configuration of multiple communication structures.

10. The device according to claim 9, wherein using the opened CANopen structure communication object identifications of the apparatuses establish a logical double ring bus structure.

11. The device according to claim 9, wherein using the opened CANopen structure communication object identifications of the apparatuses establish a logical ring-star bus structure.

12. The device according to claim 9, wherein using the opened CANopen structure communication object identifications of the apparatuses establish a logical ring-ring bus structure.

13. The device according to claim 9, wherein using the CANopen structure nodes of individual rings are logically connected to form a common ring.

\* \* \* \* \*